United States Patent [19]

Yoshioka et al.

[11] Patent Number: 5,264,103
[45] Date of Patent: Nov. 23, 1993

[54] BIOSENSOR AND A METHOD FOR MEASURING A CONCENTRATION OF A SUBSTRATE IN A SAMPLE

[75] Inventors: Toshihiko Yoshioka, Osaka; Shiro Nankai, Hirakata both of Japan

[73] Assignee: Matsushita Electric Industrial Co., Ltd., Osaka, Japan

[21] Appl. No.: 961,528

[22] Filed: Oct. 15, 1992

[30] Foreign Application Priority Data

| Oct. 18, 1991 [JP] | Japan | 3-270839 |
| Oct. 21, 1991 [JP] | Japan | 3-272293 |
| Apr. 9, 1992 [JP] | Japan | 4-088507 |

[51] Int. Cl.⁵ .............................. G01N 27/26
[52] U.S. Cl. .............................. 204/403; 204/412; 204/418; 435/817
[58] Field of Search ................ 204/403, 412, 418; 435/817

[56] References Cited

U.S. PATENT DOCUMENTS

| 5,120,420 | 6/1992 | Nankai et al. | 204/403 |
| 5,192,415 | 3/1993 | Yoshioka et al. | 204/403 |

FOREIGN PATENT DOCUMENTS 63-121002 11/1989 Japan .
1-291153 11/1989 Japan .

*Primary Examiner*—John Niebling
*Assistant Examiner*—Bruce F. Bell
*Attorney, Agent, or Firm*—Renner, Otto, Boisselle & Sklar

[57] ABSTRACT

The present invention provides a biosensor comprising an electrical insulating substrate, a main electrode system formed on the substrate and having a working electrode and a counter electrode, a reaction layer provided in contact with or in the vicinity of the main electrode system and containing an oxidoreductase, and a sub electrode system as a reference provided with an interval from the main electrode system and having a working electrode and a counter electrode.

13 Claims, 4 Drawing Sheets

BIOSENSOR AND A METHOD FOR MEASURING A CONCENTRATION OF A SUBSTRATE IN A SAMPLE

BACKGROUND OF THE INVENTION

1. Field of the Invention

The present invention relates to a biosensor that can easily quantify a specific component in a sample liquid with speed and accuracy, and a method for measuring a concentration of a substrate (a specific component) in a sample by using the biosensor. More particularly, it relates to a biosensor that can quantify a specific component in a sample liquid by reacting the specific component in the sample liquid to an oxidoreductase that specifically reacts to the component and then by quantifying the change of concentration of a material that has changed through the reaction after a predetermined period of time, and to a method for measuring the concentration of a substrate in a sample by using the biosensor.

2. Description of the Prior Art

Various types of biosensors utilizing specific catalyses of enzyme have been recently developed. A saccharide biosensor will be described as an example of such biosensors as follows:

The optical rotation method, the colorimetric method, the reductimetry method and other methods using different kinds of chromatographies have been developed as methods for quantitative analysis of saccharides. However, none of these methods can provide high accuracy due to the relatively low specificity against saccharides. Additionally, the optical rotation method is easy to operate but is largely influenced by the operating temperature. Therefore, it is not appropriate for common use at home and the like.

The saccharides contained in fruit are generally assessed as saccharine degrees. A refractometer of the light refraction system is often used for quantifying the saccharine degree. This refractometer functions by utilizing change of the light refractive index caused by liquid concentration. Therefore, the refractometer of the light refraction system is influenced by all the components dissolved in the sample liquid, for example, by organic acid such as citric acid or maleic acid that is contained in fruit juice in large amounts when a saccharide in the fruit is quantified. Thus, accurate quantification by this refractometer is impossible.

A glucose sensor will now be described as an example of a biosensor used in a clinical field.

A conventional method for quantifying glucose contained in blood is to centrifuge blood taken from a patient and then to measure the thus obtained blood plasma. This method requires a lot of time as well as labor. Therefore, a sensor that can directly measure glucose in blood obtained from a patient is desired.

A sensor similar to a test paper for urinalysis has been developed as a simple glucose sensor. This glucose sensor comprises a support in a stick shape and a holder fixed to the support. The holder includes an enzyme reacting only to glucose and a dye, the color of which is changed by reacting with a production of the enzyme reaction. Blood is dropped onto the support of the glucose sensor and the change of the color of the dye after a predetermined period of time of the dropping is visually observed or optically measured, whereby the content of glucose in the blood can be measured. However, the quantifying method using this glucose sensor has low accuracy due to interference by the colored materials in the blood.

Japanese Laid-Open Patent Publication No. 1-291153 discloses the following glucose sensor with high accuracy as a method for quantifying a specific component in a sample liquid from a living body such as blood without diluting or stirring the sample liquid:

The biosensor comprises a base 42, and a spacer 3 and a cover 4 that are laminated integrally onto the base 42 as is shown in FIGS. 13 and 14.

The base 42 comprises an electrical insulating substrate 1, an electrode system 43 formed on the substrate 1 by screen printing, etc. and a reaction layer 44 provided on the electrode system 43. The electrode system 43 includes a working electrode 45 and a counter electrode 46 that are electrically insulated from each other by an insulating layer 47. The working electrode 45 and the counter electrode 46 are connected to leads 12 and 13 formed on the substrate 1, respectively.

The reaction layer 44 includes a hydrophilic polymer, an oxidoreductase and electron acceptors and covers the working electrode 45 and the counter electrode 46.

As is shown in FIG. 13, the spacer 3 is in a U-shape and has a groove 17. When the spacer 3 and the cover 4 are laminated on the base 42, a passage 18 through which a sample liquid passes is formed between the base 42 and the cover 4 as is shown in FIG. 14. One end of the passage 18 is open at one end of the base 42 and the opening serves as a sample supply port 23. The other end of the passage 18 is open on the cover 4 and the opening serves as an air port 24.

The operation of the glucose sensor with the above-mentioned structure is as follows: A sample liquid supplied through the sample supply port 23 reaches the reaction layer 44 through the passage 18 and the oxidoreductase and the electron acceptors contained in the reaction layer 44 are dissolved in the sample liquid. Thus, while an enzyme reaction is proceeded between a substrate in the sample liquid and the oxidoreductase, the electron acceptors are reduced. After finishing the enzyme reaction, the reduced electron acceptors are electrochemically oxidized. A value of an oxidation current obtained at this point provides a concentration of the substrate in the sample liquid.

However, the conventional biosensor has the following disadvantages:

The sample liquid may include reductive materials that can reduce the electron acceptors other than the substrate to be measured. Moreover, viscosity, etc. of the sample liquid to be measured vary.

Accordingly, in measuring a concentration of the substrate in the sample liquid including the substrate and another reductive material that can reduce the electron acceptors, the response values of the sensor are inconstant, and therefore, the reductive material should be eliminated before the measurement. Such a pretreatment results in increasing the number of steps in measuring the concentration of a substrate in a sample liquid.

Moreover, the sensor response also depends upon a measuring time. For example, an accurate concentration can not be obtained when the oxidation current is measured before completely finishing the reaction.

Furthermore, time required for the sample liquid to reach the reaction layer and the rate of the reaction of the substrate to the enzyme depends upon the viscosity of the sample liquid. Therefore, the inconstant viscosities result in inconstant sensor responses.

SUMMARY OF THE INVENTION

The biosensor of this invention comprises an electrical insulating substrate, a main electrode system formed on the substrate and having a working electrode and a counter electrode, a reaction layer provided in contact with or in the vicinity of the main electrode system and containing an oxidoreductase, and a sub electrode system as a reference provided with an interval from the main electrode system and having a working electrode and a counter electrode.

In another aspect of the present invention, the biosensor comprises an electrical insulating substrate, a main electrode system formed on the substrate and having a working electrode and a counter electrode, a reaction layer provided on the main electrode system and containing an oxidoreductase and electron acceptors, and a sub electrode system as a reference provided with an interval from the main electrode system and the reaction layer and having a working electrode and a counter electrode, wherein a substrate contained in a sample liquid is quantified by reducing the electron acceptors by electrons generated in a reaction of the substrate contained in the sample liquid and the oxidoreductase and then by electrochemically measuring the amount of the reduced electron acceptors.

In another aspect of the present invention, the biosensor comprises an electrical insulating substrate having a plurality of surfaces, a plurality of electrode systems formed on at least two surfaces of the substrate, each of the electrode systems having a working electrode and a counter electrode, and a plurality of reaction layers containing an oxidoreductase, respectively, wherein the electrode systems are respectively provided on different surfaces of the substrate from each other, and the reaction layers are provided on the same surfaces as the electrode systems.

Alternatively, the present invention provides a method for quantifying a substrate contained in a sample liquid by using a biosensor. The biosensor comprises an electrical insulating substrate, a main electrode system formed on the substrate and having a working electrode and a counter electrode, a reaction layer provided in contact with or in the vicinity of the main electrode system and containing an oxidoreductase, and a sub electrode system as a reference provided on the substrate with an interval from the main electrode system and having a working electrode and a counter electrode. The method comprises the steps of detecting a presence of the sample liquid on the both the electrode systems by detecting a change of electrical characteristics between the main electrode system and the sub electrode system and then applying a voltage to the main electrode system and a sub electrode system, respectively.

Alternatively, the present invention provides a method for quantifying a substrate contained in a sample liquid by using a biosensor. The biosensor comprises an electrical insulating substrate, a main electrode system formed on the substrate and having a working electrode and a counter electrode, a reaction layer provided in contact with or in the vicinity of the main electrode system and containing an oxidoreductase, and a sub electrode system provided on the substrate with an interval from the main electrode system and having a working electrode and a counter electrode. The method comprises the steps of detecting a change of electrical characteristics between the working electrode and the counter electrode in the main electrode system and the sub electrode system, respectively and determining a nature of the sample liquid on the basis of the difference of time required for detecting the electrical characteristics in the main and sub electrode systems.

Thus, the invention described herein makes possible the advantages of (1) providing a biosensor for quantifying a specific substrate contained in a sample liquid easily, rapidly and accurately, (2) providing a biosensor that conducts an accurate measurement without a pretreatment for removing a material in a sample liquid that disturbs a sensor response, and (3) providing a method for quantifying a substrate contained in a sample liquid in which constant sensor responses are obtained regardless of viscosity of the sample liquid.

These and other advantages of the present invention will become apparent to those skilled in the art upon reading and understanding the following detailed description with reference to the accompanying figures.

DESCRIPTION OF THE PREFERRED EMBODIMENTS

Figure 1:
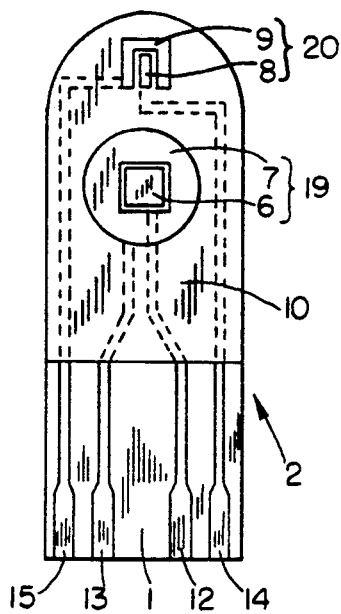
FIG. 1 is a plan view of a base of a glucose sensor according to an example of the present invention.

Throughout the drawings mentioned in the following description of the examples, the same element has a common reference numeral. Part of the description is omitted as occasion demands.

EXAMPLE 1

A glucose sensor will now be described as an example of a biosensor according to the present invention.

Figure 2:
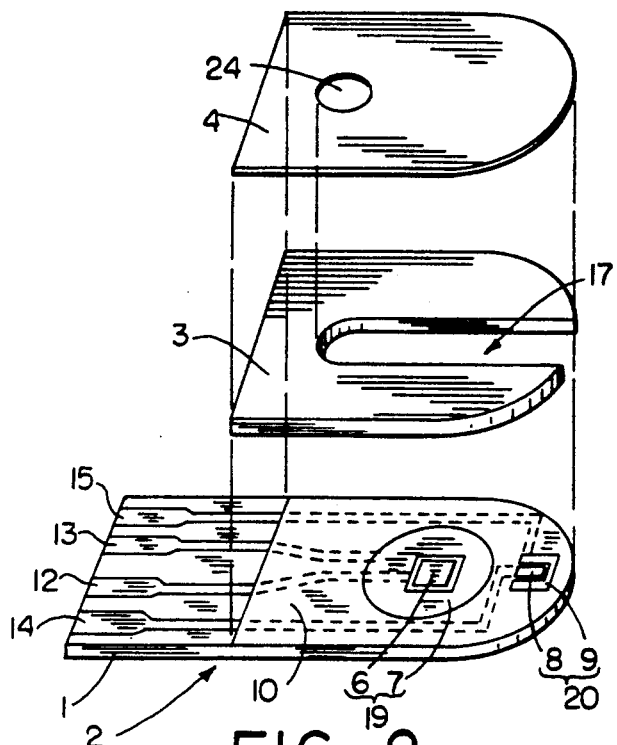
FIG. 2 is an exploded perspective view of the glucose sensor of FIG. 1 from which a reaction layer is removed.
Figure 3:
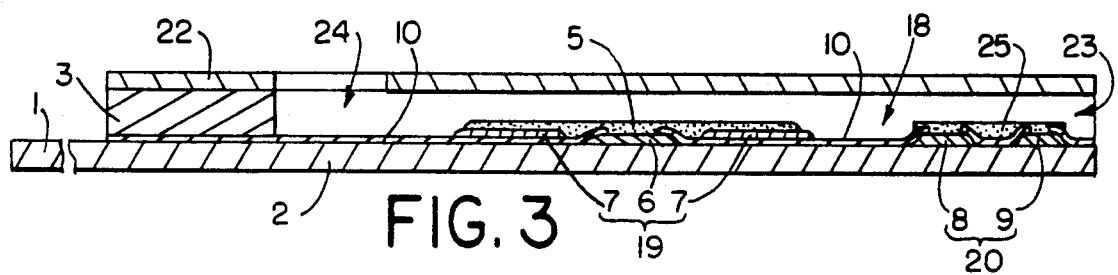
FIG. 3 is a sectional view of the glucose sensor of FIG. 1.

The glucose sensor comprises a base 2, and a spacer 3 and a cover 4 integrally laminated on the base 2 as is shown in FIGS. 2 and 3.

The base 2 comprises an electrical insulating substrate 1 made from polyethylene terephthalate, an electrode system formed on the substrate 1 by screen printing and the like. The electrode system comprises a main electrode system 19 and a sub electrode system 20 provided on the substrate 1 with an interval therebetween. The main electrode system 19 and the sub electrode system 20 include working electrodes 6 and 8 and counter electrodes 7 and 9, respectively. The working electrodes 6 and 8 and the counter electrodes 7 and 9 are electrically insulated from each other by an insulating layer 10.

A lead 12 formed on the substrate 1 is electrically connected to the working electrode 6 of the main electrode system 19, a lead 13 to the counter electrode 7 of the main electrode system 19, a lead 14 to the working electrode 8 of the sub electrode system 20, and a lead 15 to the counter electrode 9 of the sub electrode system 20.

A reaction layer 5 covers the working electrode 6 and the counter electrode 7 of the main electrode system 19. The reaction layer 5 includes carboxy methyl cellulose (hereinafter called the CMC) as a hydrophilic polymer, glucose oxidase (EC1.1.3.4; hereinafter called the GOD) as an oxidoreductase, and potassium ferricyanide as electron acceptors.

As is shown in FIG. 2, the spacer 3 is formed in a U-shape and has a groove 17 that is open at one end thereof. When the spacer 3 and the cover 4 are laminated on the base 2, a passage 18 through which a sample liquid passes is formed between the base 2 and the cover 4. One end of the passage 18 is open at one end of the base 2, and the opening serves as a sample supply port 23. The other end of the passage 18 is open on the cover 4, and the opening serves as an air port 24. Accordingly, the reaction layer 5 is provided between the air port 24 and the sample supply port 23 so as to face the passage 18.

The glucose sensor was produced as follows: Silver paste was printed on the substrate 1 by means of screen printing to form the leads 12, 13, 14 and 15. Then conductive carbon paste including resin binder was printed on the substrate 1 to form the working electrode 6 of the main electrode system 19 and the working electrode 8 and the counter electrode 9 of the sub electrode system 20.

The working electrodes 6 and 8 and the counter electrode 9 were electrically connected to the leads 12, 14 and 15, respectively.

Next, insulating paste was printed on the substrate 1 to form the insulating layer 10. The insulating layer 10 covered the peripheral portion of the working electrode 6 so that a predetermined area of the working electrode 6 was exposed. Further, the insulating layer 10 covered a part of the leads 12, 13, 14 and 15, respectively. The working electrode 8 and the counter electrode 9 of the sub electrode system 20 were partly covered by the insulating layer 10 so that a predetermined area of the working electrode 8 and the counter electrode 9 were respectively exposed.

Then, conductive carbon paste including resin binder was printed on the insulating layer 10 so as to come in contact with the lead 13 to form the counter electrode 7 of the main electrode system 19. The base 2 shown in FIG. 1 was produced in this manner.

Next, an aqueous solution including the GOD as the oxidoreductase, potassium ferricyanide as the electron acceptors and the 0.5 wt % of CMC as the hydrophilic polymer was dropped on the working electrode 6 and the counter electrode 7 of the main electrode system 19, and was dried in a warm-air drier at a temperature of 50° C. for 10 minutes to form the reaction layer 5. The reaction layer 5 can be easily formed in this manner.

Then, a mixed aqueous solution including potassium ferricyanide and the CMC was dropped onto the working electrode 8 and the counter electrode 9 of the sub electrode system 20 and dried to form a reference layer 25.

After forming the reaction layer 5 and the reference layer 25 on the substrate 1, the cover 4 and the spacer 3 were laminated to be adhered onto the base 2 as shown in FIG. 2 with dashed lines. Thus, the passage 18 having a comparatively small cross section was formed which was defined by the groove 17 of the spacer 3, the cover 4 and the base 2.

The thus produced glucose sensor was supplied with 3 $\mu$l of a mixed aqueous solution including glucose and ascorbic acid as a sample liquid through the sample supply port 23. Before the supply of the sample liquid, the entire biosensor including the reference layer 25 and the reaction layer 5 was in a dry condition. The sample liquid coming in contact with the sample supply port 23 at the tip of the sensor is introduced into the passage 18 by capillarity. Thus, the sample liquid is introduced into the sub electrode system 20 and the reaction layer 5 by simply allowing the sample liquid to come into contact with the sample supply port 23.

The sample liquid reached the air port 24 through the sub electrode system 20 due to capillarity, and the reference layer 25 on the sub electrode system 20 and the reaction layer 5 on the main electrode system 19 were respectively dissolved in the sample liquid. At the same time, an impedance between the working electrode 6 of the main electrode system 19 and the working electrode 8 of the sub electrode system 20 was changed. The impedance change showed a sufficient supply of the sample liquid to the sensor. Next, a voltage of $+0.5$ V on the basis of the voltage at the counter electrode 9 of the sub electrode system 20 was applied to the working electrode 8. An oxidation current (an anodic current) value $I_0$ of five seconds after the application was measured.

The potassium ferricyanide on the sub electrode system 20 was reduced by ascorbic acid in the sample liquid to generate potassium ferrocyanide. The oxidation current value $I_0$ obtained by the application of the above-mentioned predetermined voltage was caused by oxidation of the potassium ferrocyanide. Therefore, the oxidation current value $I_0$ was in proportion to the amount of ascorbic acid contained in the sample liquid.

A voltage of $+0.5$ V on the basis of the voltage at the counter electrode 7 of the main electrode system 19 was applied to the working electrode 6 of the main electrode system 19 one minute after detecting the above described impedance change. An oxidation current value $I_1$ of five seconds after the application was measured.

The oxidation current value $I_1$ is a total value of a current caused by oxidation of potassium ferrocyanide generated by reduction by ascorbic acid and one caused by oxidation of potassium ferrocyanide generated in oxidizing glucose by the GOD.

When a coefficient for correcting the difference in the responses in both the electrode systems is taken as k, a current value represented as $I_1 - kI_0$ closely corresponded to the glucose concentration in the sample liquid.

Next, responses obtained in the following operations (1) and (2) were compared, using thirty glucose sensors.

(1) After supplying the sample liquid to the sensor through the sample supply port, a sufficient supply of the sample liquid to the reaction layer 5 was detected by detecting the change of the electrical characteristics between the main electrode system and the sub electrode system. Then the sensor responses were obtained in the above-mentioned manner.

(2) Instead of the detection of the change in the electrical characteristics, sufficient supply of the sample liquid to the reaction layer 5 was confirmed by visual observation. Then the sensor responses were obtained by measuring the oxidation currents value $I_0$ and $I_1$ in the same manner as above.

As a result, a coefficient of variation (a CV value) showing the dispersion of the responses was 2% in operation (1) and 5% in operation (2).

As mentioned above, the coefficient of the variation in operation (1) was smaller than that in operation (2). This seems to be because the inconstancy in time from the measurement of the response current in the sub electrode system to that in the main electrode system was made smaller in operation (1).

In this example, the GOD in the reaction layer 5 was not immobilized in the main electrode system 19. However, since the reaction layer 5 contained the hydrophilic polymer, the viscosity of the sample liquid was enhanced when the reaction layer 5 was dissolved in the sample liquid. Therefore, dispersion of materials contained in the reaction layer 5 was prevented so that the materials did not move toward the sub electrode system 20 in a short period of time. A more accurate measurement can be effectively attained by immobilizing an enzyme such as the GOD in the main electrode system 19.

EXAMPLE 2

Figure 4:
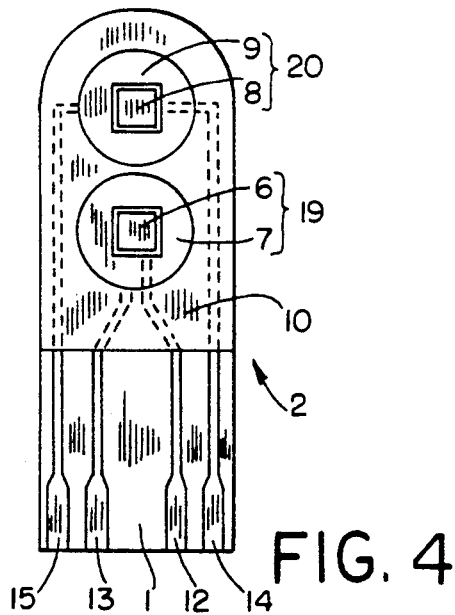
FIG. 4 is a plan view of a base of a glucose sensor according to another example of the present invention.

FIG. 4 is a plan view of a base 2 of a glucose sensor produced as another example of the biosensor according to the present invention. This glucose sensor was produced as follows:

Silver paste was printed on an electrical insulating substrate 1 made from polyethylene terephthalate by screen printing to form leads 12, 13, 14 and 15. Next, conductive carbon paste including resin binder was printed on the substrate 1 to form a working electrode 6 of a main electrode system 19 and a working electrode 8 of a sub electrode system 20.

The working electrodes 6 and 8 were electrically connected to the leads 12 and 14, respectively.

Insulating paste was then printed on the substrate 1 to form an insulating layer 10. The insulating layer 10 covered peripheral portions of the working electrodes 6 and 8 so that a predetermined area of the working electrodes 6 and 8 was exposed, respectively. Moreover, the insulating layer 10 covered a part of the leads 12, 13, 14 and 15, respectively.

Next, conductive carbon paste including resin binder was printed on the insulating layer 10 so as to come in contact with the leads 13 and 15 to form a counter electrode 7 of the main electrode system 19 and a counter electrode 9 of the sub electrode system 20. In this manner, the base 2 shown in FIG. 4 was produced.

A mixed aqueous solution including the GOD, potassium ferricyanide and the CMC was dropped on the working electrode 6 and the counter electrode 7 of the main electrode system 19 in the same manner as in Example 1. A mixed aqueous solution including bovine serum albumin (hereinafter called the BSA), potassium ferricyanide and the CMC was then dropped on the working electrode 8 and the counter electrode 9 of the sub electrode system 20, and dried in a warm-air drier at a temperature of 50° C. for 10 minutes, to form a reaction layer and a reference layer (not shown) on the main electrode system 19 and the sub electrode system 20, respectively.

Then a spacer 3 and a cover 4 were laminated integrally on the base 2 having the reaction layer and the reference layer in the same manner as in Example 1, to form the glucose sensor.

Since the reference layer comprising the BSA, potassium ferricyanide and the CMC is formed on the sub electrode system 20, conditions for diffusion of a reductive material such as ascorbic acid on the sub electrode system 20 and the like, are similar to those on the main electrode system 19.

In the case that proteins such as the GOD and the BSA exist on the electrode systems, the activity of the electrodes may be partly degraded by absorption of such proteins. However, a layer including proteins provided on both the main and sub electrode systems 19 and 20 as described above can minimize errors in the oxidation current values detected in each electrode system due to the absorption of the proteins. As a result, the correction between the oxidation current values in both the electrode systems 19 and 20 can be simplified.

Such an advantage is especially remarkable in a sensor using carbon as a main electrode material.

EXAMPLE 3

Next, a fructose sensor as an example of a biosensor will be described.

Figure 5:
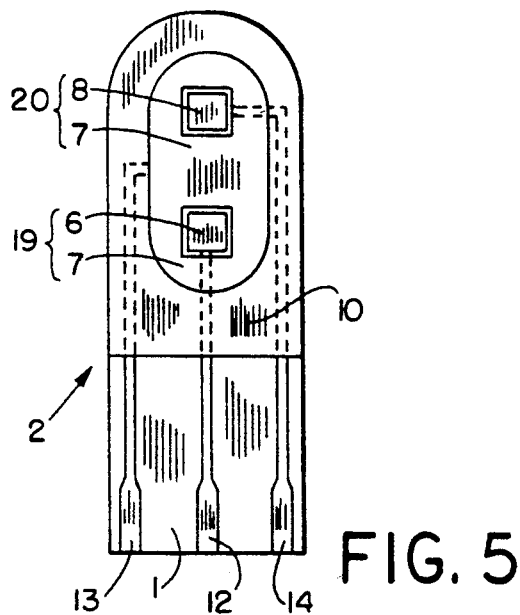
FIG. 5 is a plan view of a base of a glucose sensor according to still another example of the present invention.

FIG. 5 is a plan view of a base 2 of a fructose sensor produced as still another example of the biosensor according to the present invention. The fructose sensor was produced as follows:

As is shown in FIG. 5, silver paste was printed on an electrical insulating substrate 1 made from polyethylene terephthalate by screen printing to form leads 12, 13 and 14. Next, conductive carbon paste including resin binder was printed on the substrate 1 to form a working electrode 6 of a main electrode system 19 and a working electrode 8 of a sub electrode system 20. An insulating layer 10 was then formed on the substrate 1 by using insulating paste. The insulating layer 10 covered propheral portions of the working electrodes 6 and 8 so that a predetermined area of the working electrodes 6 and 8 was respectively exposed. Further, the insulating layer 10 covered a part of the leads 12, 13 and 14, respectively.

Next, conductive carbon paste including resin binder was printed on the insulating layer 10 so as to come in contact with the lead 13 to form a counter electrode 7. Thus the base 2 was produced.

Next, a mixed aqueous solution of fructose dehydrogenase (EC1.1.99.11; hereinafter called the FDH) as an oxidoreductase, potassium ferricyanide as electron acceptors and the CMC as a hydrophilic polymer in a phosphate buffer solution (pH=5) was dropped on the working electrode 6 and the counter electrode 7 of the main electrode system 19, and dried in a warm-air drier at a temperature of 40° C. for 10 minutes to form a reaction layer (not shown).

A spacer and a cover were laminated integrally on the thus obtained base 2 in the same manner as in Example 1 to produce the fructose sensor.

Three μl of a mixed aqueous solution of fructose and ascorbic acid was supplied to the fructose sensor. A voltage of +1 V on the basis of the counter electrode 7 was applied to the working electrode 8 of the sub electrode system 20 and an oxidation current value $I_0$ was measured. Since no oxidoreductase and electron acceptors existed on the working electrode 8 of the sub electrode system 20, the current value $I_0$ was an oxidation current value of ascorbic acid contained in the sample liquid. Moreover, since no hydrophilic polymer and the like for preventing diffusion of materials existed on the sub electrode system, an accurate current value $I_0$ was obtained immediately after the supply of the sample liquid. The current value $I_0$ was in proportion to the ascorbic acid concentration.

Moreover, a voltage of +0.5 V on the basis of the counter electrode 7 was applied to the working electrode 6 of the main electrode system 19 one minute after the supply of the sample liquid to the sensor through the sample supply port. A current value $I_1$ of 5 seconds after the application was measured. The current value $I_1$ is a total value of an oxidation current of potassium ferrocyanide generated by a reaction with ascorbic acid and one generated in a reduction of fructose by the FDH.

The amount of ascorbic acid contained in the sample liquid was quantified by using the current value $I_0$. A fructose concentration in the sample liquid was calculated from the quantified amount of ascorbic acid and the amount of potassium ferrocyanide quantified with the current value $I_1$.

In the fructose sensor according to this example, the counter electrode 7 serves as a common counter electrode to the main and sub electrode systems 19 and 20. The production of the sensor can be simplified by using the counter electrode in common in this manner. Moreover, the cost for producing the sensor can be reduced by using one less lead. In addition, inequality of the surfaces of the electrode systems on the substrate 1 can be minimized, thereby preventing the reaction layer from peeling off from the electrode systems. As a result, a sensor with excellent conservative and stable properties can be produced, and an accurate sensor response can be obtained by making the movement of the sample liquids smoother on the electrode systems.

EXAMPLE 4

A method for measuring a glucose concentration in whole blood by using the glucose sensor produced in the same manner as in Example 1 will now be described.

Whole blood was supplied to the glucose sensor through the sample supply port 23. The entire glucose sensor including the reaction layer 5 was in a dry condition before the supply of the sample liquid. The sample liquid, that is, the whole blood reached the sub electrode system 20 first, thereby reducing an impedance between the working electrode 8 and the counter electrode 9 in the sub electrode system 20. The impedance change was detected through the leads 14 and 15.

Next, the whole blood reached the main electrode system 19. When the reaction layer 5 on the main electrode system 19 was dissolved, an impedance between the working electrode 6 and the counter electrode 7 of the main electrode system 19 was reduced. The impedance change was detected through the leads 12 and 13.

When the reaction layer 5 was dissolved in the whole blood, the glucose in the blood was oxidized by the GOD, and at the same time potassium ferricyanide was reduced into potassium ferrocyanide. One minute after the supply of the whole blood to the glucose sensor, a voltage of +0.5 V on the basis of the counter electrode 7 was applied to the working electrode 6, and an oxidation current 5 seconds after the application was measured. The obtained current value was due to the reduction of potassium ferrocyanide and was in proportion to the concentration of glucose, the substrate to be measured.

When the above described oxidation current values were measured by using the whole blood sample with a hematocrit of 20% to 60%, a higher hematocrit reduced the oxidation current value. Moreover, when the difference of time required for detecting the impedance change between the main electrode system and the sub electrode system was taken as t, the t increased proportionally to the increase of the hematocrit in using the whole blood with a hematocrit of 20% to 60%.

When values obtained by correcting the oxidation current value with the above factor t were taken as sensor responses, the sensor responses were constant regardless of the hematocrit value in the whole blood sample and corresponded to the glucose concentration in the whole blood.

In this example, the sample liquid can be supplied through the air port 24, using the sample supply port 23 as an air port. In this case, the impedance change is first detected in the main electrode system, and then in the sub electrode system. The difference in time t2 required for detecting the impedance change between the main electrode system and the sub electrode system does not necessarily correspond to the above t. However, the same effect as in this example can be attained by studying the relation between t2 and the hematocrit previously.

EXAMPLE 5

A glucose sensor will now be described as an example of the biosensor according to the present invention.

Figure 6:
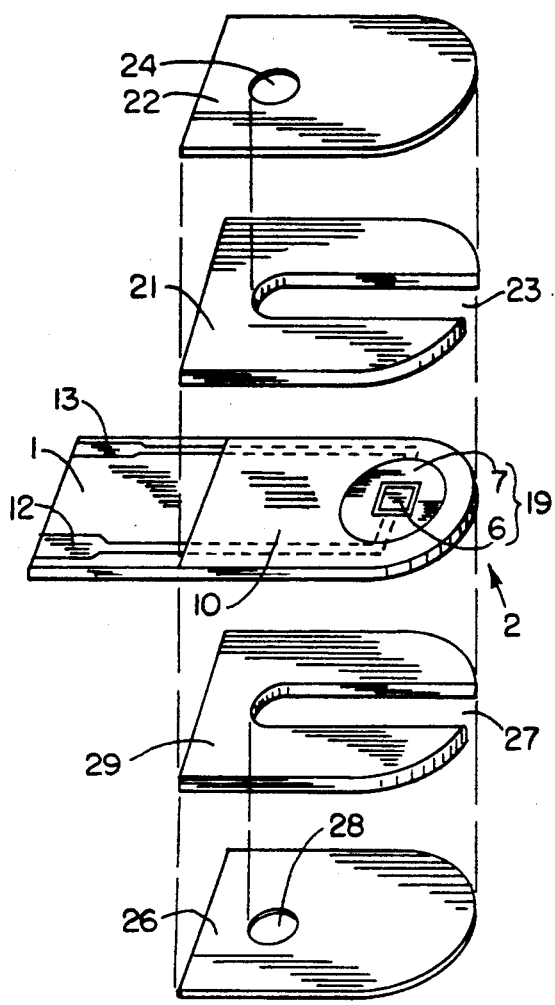
FIG. 6 is an exploded perspective view seen from one side of a glucose sensor according to still another example of the present invention.
Figure 7:
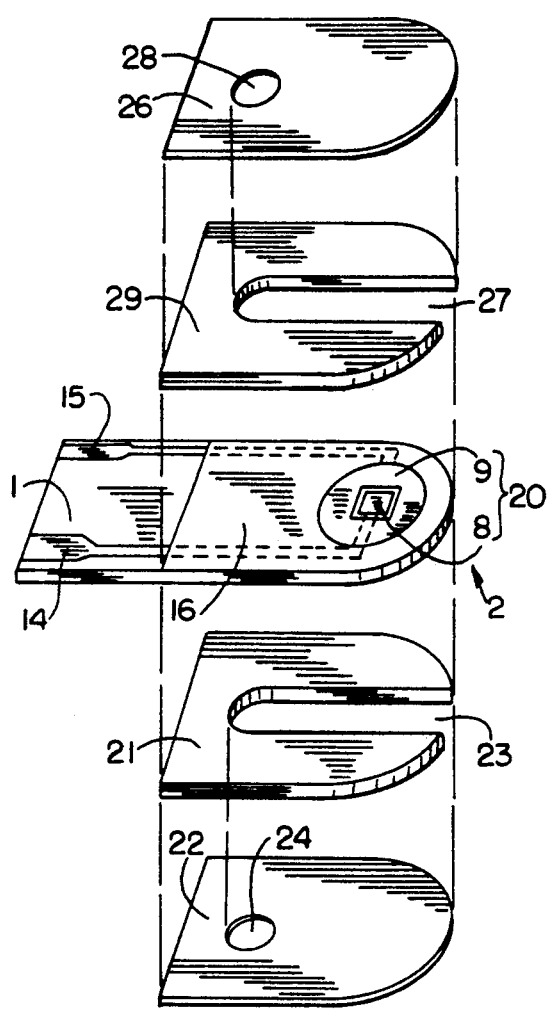
FIG. 7 is an exploded perspective view of the glucose sensor of FIG. 6 seen from the other side.
Figure 8:
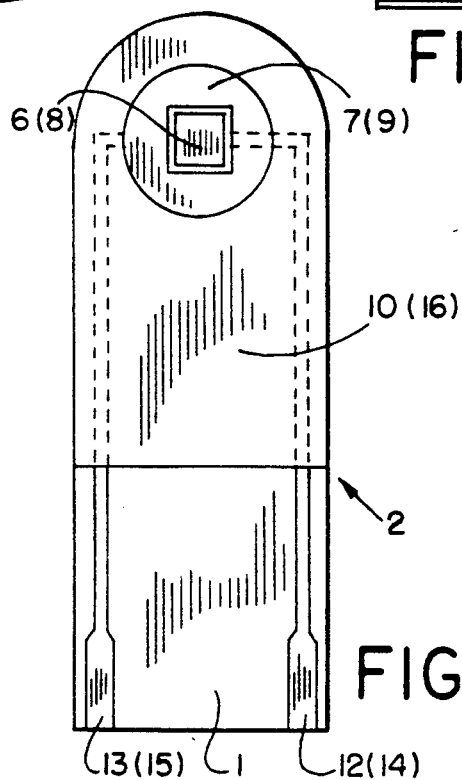
FIG. 8 is a plan view of a base of the glucose sensor of FIG. 6.
Figure 9:
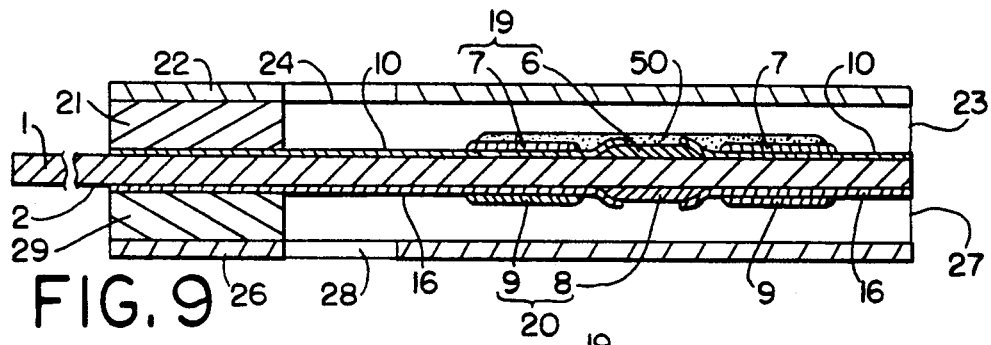
FIG. 9 is a sectional view of the glucose sensor of FIG. 6.

FIG. 6 is an exploded perspective view of the glucose sensor seen from one side from which a reaction layer 50 is removed. FIG. 7 is an exploded perspective view of the glucose sensor seen from the other side from which a reaction layer 50 is removed. FIG. 8 is a plan view of a base 2 of the glucose sensor produced in this example. FIG. 9 is a sectional view of the glucose sensor produced in this example.

A method for producing the glucose sensor will now be described.

Silver paste was printed on a substrate 1 made from polyethylene terephthalate by screen printing to form leads 12 and 13. Next, conductive carbon paste including resin binder was printed on the substrate 1 to form a working electrode 6 of a main electrode system 19. The working electrode 6 was electrically connected to the lead 12. Insulating paste was then printed on the substrate 1 to form an insulating layer 10. The insulating layer 10 covered the peripheral portion of the working electrode 6 so that a predetermined area of the working electrode 6 was exposed.

Next, conductive carbon paste including resin binder was printed on the insulating layer 10 so as to come in contact with the lead 13 to form a counter electrode 7 of the main electrode 19.

On the reverse surface of the insulating substrate 1 on which the above-mentioned electrode pattern was printed, leads 14 and 15, a sub electrode system 20 (including a working electrode 8 and a counter electrode 9) and an insulating layer 16 were formed by printing, thereby producing the base 2 as shown in FIGS. 7 and 8.

The structures of the main electrode system 19 and the sub electrode system 20 were the same, and therefore, the areas of the working electrodes 6 and 8 were also the same.

A mixed aqueous solution including the GOD as the oxidoreductase, potassium ferricyanide as the electron acceptors and the CMC as the hydrophilic polymer was dropped on the main electrode system 19, and dried in a warm-air drier at a temperature of 50° C. for 10 minutes to form a reaction layer 50.

Next, spacers 21 and 29 and covers 22 and 26 were laminated to adhere to the base 2 having the above-described reaction layer 50 as shown in FIG. 9, to produce the glucose sensor.

To the thus obtained glucose sensor, 10 μl of a mixed aqueous solution of glucose and ascorbic acid as a sample liquid was supplied through sample supply ports 23 and 27. The supplied sample liquid immediately reached air ports 24 and 28 due to capillarity, and the reaction layer 50 on the main electrode system 19 was dissolved.

A voltage of +1 V on the basis of the counter electrode 9 of the sub electrode system 20 was then applied to the working electrode 8, and the current value $I_0$ was measured. Since no oxidoreductase and electron acceptors existed on the sub electrode system 20, the current value $I_0$ was a value of an oxidation current of ascorbic acid in the sample liquid. Moreover, since no hydrophilic polymer for preventing dispersion of materials existed on the sub electrode system 20, the current value $I_0$ was obtained immediately after the supply of the sample liquid. The current value $I_0$ was in proportion to the concentration of ascorbic acid.

One minute after the supply of the sample liquid, a voltage of +0.5 V on the basis of the counter electrode 7 of the main electrode system 19 was applied to the working electrode 6 of the main electrode system 19, and the current value $I_1$ after 5 seconds of the application was measured. The current value $I_1$ was a total value of an oxidation current of potassium ferrocyanide generated by a reaction to ascorbic acid and one generated in a reduction of glucose by the GOD.

The amount of ascorbic acid in the sample liquid was quantified from the current value $I_0$. A glucose concentration in the sample liquid was calculated from the quantified amount of ascorbic acid and the amount of potassium ferrocyanide obtained from the current value $I_1$.

In this example, the main electrode system 19 and the sub electrode system 20 were provided on different sides from each other. Accordingly, the materials contained in the reaction layer 50 such as the GOD did not move onto the sub electrode system 20. As a result, there was no need to immobilize the GOD, potassium ferricyanide and the like to the main electrode system 19.

Figure 10:
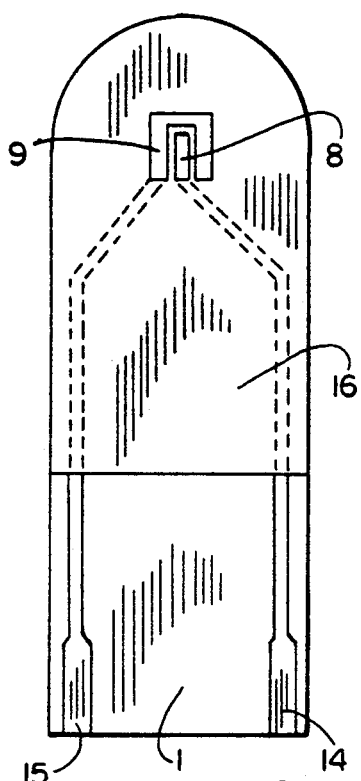
FIG. 10 is a plan view of a base of a glucose sensor according to still another example of the present invention.
Figure 13:
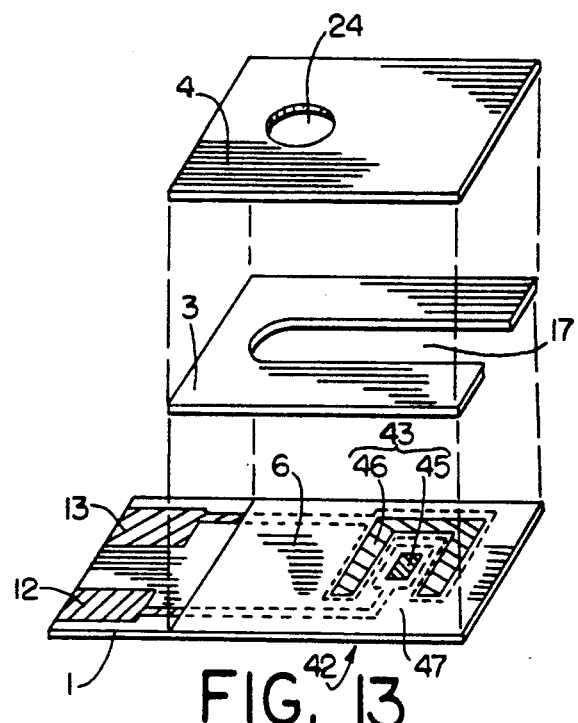
FIG. 13 is an exploded perspective view of a conventional disposable glucose sensor from which a reaction layer is removed.

Apart from in the above-mentioned method, the base 2 can be produced by laminating two insulating substrates 1 respectively bearing an electrode pattern on one surface thereof to each other. The structure of the sub electrode system does not necessarily correspond to that of the main electrode system. For example, the structure shown in FIG. 10 can be used.

EXAMPLE 6

Figure 11:
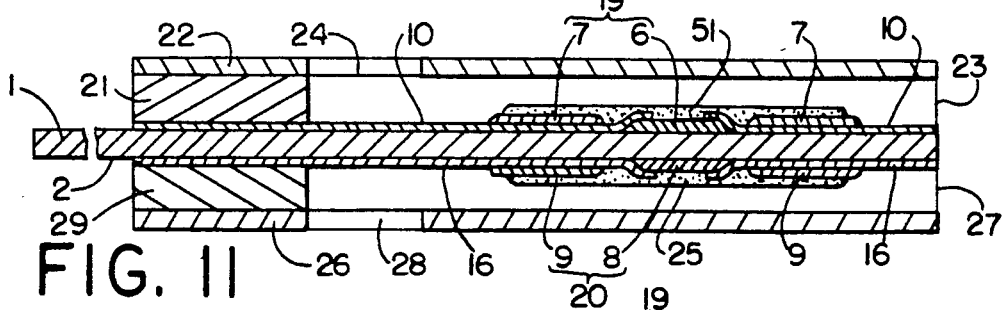
FIG. 11 is a sectional view of a glucose sensor according to still another example of the present invention.

FIG. 11 is a sectional view of a glucose sensor produced as yet another example of the present invention.

A base 2 was produced in the same manner as in Example 5.

A mixed aqueous solution of the GOD, potassium ferricyanide and the CMC was dropped on a main electrode system 19 (a working electrode 6 and a counter electrode 7) of the base 2 and dried to form a reaction layer 51 in the same manner as in Example 5. Next, a mixed aqueous solution of potassium ferricyanide and the CMC was dropped onto a sub electrode system 20 (a working electrode 8 and a counter electrode 9) and dried to form a reference layer 25 made from potassium ferricyanide and the CMC.

A spacer 3 and a cover 4 were integrally laminated on the base 2 in the same manner as in Example 5 to form the glucose sensor.

To the thus obtained glucose sensor, 10 μl of a mixed aqueous solution of glucose and ascorbic acid as a sample liquid was supplied through sample supply ports 23 and 27. The sample liquid immediately reached air ports 24 and 28 due to capillarity.

The reference layer 25 was dissolved in the sample liquid on the sub electrode system 20. Pottasium ferricyanide was reduced by ascorbic acid in the sample liquid. A voltage of +0.5 V on the basis of the counter electrode 9 of the sub electrode system 20 was applied to the working electrode 8 of the sub electrode system 20 ten seconds after the supply of the sample liquid. A current value measured 5 seconds after the application was in proportion to the concentration of ascorbic acid in the sample liquid.

The reaction layer 51 was dissolved in the sample liquid on the main electrode system 19. Pottasium ferricyanide in the reaction layer 51 was changed into potassium ferrocyanide by two reactions: reduction by ascorbic acid in the sample liquid and reduction in oxidizing glucose in the sample liquid by the GOD.

A voltage of +0.5 V on the basis of the counter electrode 7 of the main electrode system 19 was applied to the working electrode 6 of the main electrode system 19 one minute after the supply of the sample liquid to the sensor. The current value $I_1$ of 5 seconds after the application was measured.

The current value $I_1$ was a total value of the oxidation current of potassium ferrocyanide generated by a reaction with ascorbic acid and one generated by a reduction in oxidizing glucose by the GOD.

A concentration of ascorbic acid in the sample liquid was quantified from the response of the sub electrode system 20. A glucose concentration in the sample liquid was calculated from the quantified ascorbic acid concentration and the amount of potassium ferrocyanide obtained from the current value $I_1$.

An output current value in the sub electrode system 20 can not be accurately measured when the GOD exists on the sub electrode system 20. The GOD can be completely prevented from moving onto the sub electrode system 20 by providing the main electrode system 19 and the sub electrode system 20 on the different surfaces of the substrate 1 from each other as in this example. As a result, a more accurate measurement can be attained.

EXAMPLE 7

A saccharide sensor will now be described as yet another example of the biosensor according to the present invention.

Figure 12:
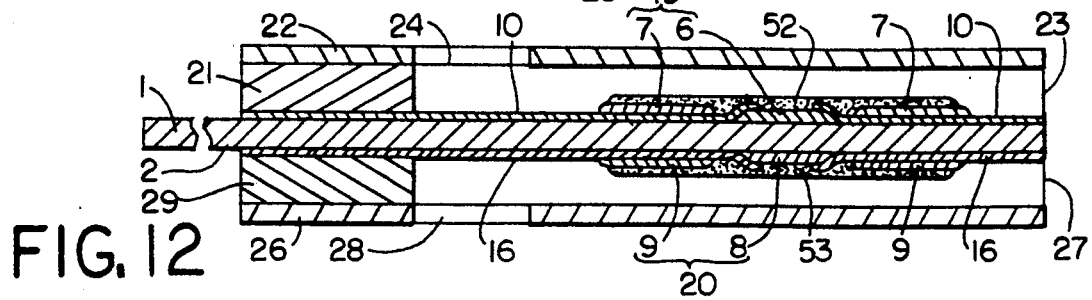
FIG. 12 is a sectional view of a saccharide sensor according to still another example of the present invention.
Figure 14:
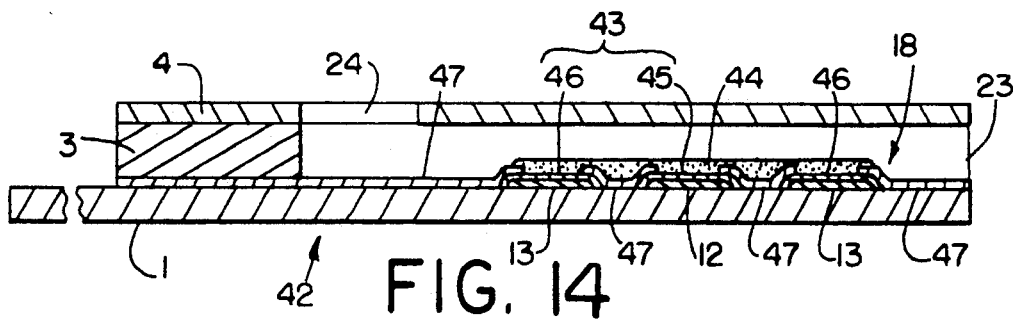
FIG. 14 is a sectional view of the glucose sensor of FIG. 13.

FIG. 12 is a sectional view of the saccharide sensor according to this example. A method for producing the saccharide sensor is as follows:

A base 2 shown in FIG. 12 was produced in the same manner as in Example 5.

Next, a mixed aqueous solution including the GOD as the oxidoreductase, potassium ferricyanide as the electron acceptors and the CMC as the hydrophilic polymer was dropped on the main electrode system 19 and dried to form a first reaction layer 52.

A mixed aqueous solution including the FDH as the oxidoreductase, potassium ferricyanide as the electron acceptors and the CMC as the hydrophilic polymer in a phosphate buffer (pH=4.5) was then dropped on the sub electrode system 20 and dried to form a second reaction layer 53. A spacer and a cover were laminated on the base 2 as in Example 5 to produce the saccharide sensor.

To the thus obtained saccharide sensor, 10 $\mu$l of glucose and fructose as a sample liquid was supplied through sample supply ports 23 and 27. A voltage of +0.5 V on the basis of the counter electrode 7 and a voltage of +0.5 V on the basis of the counter electrode 9 were applied to the working electrodes 6 and 8, respectively 2 minutes after the supply of the sample liquid. A current value at each electrode after 5 seconds was measured. In the main electrode system 19 with the first reaction layer 52, the current value corresponded to the glucose concentration. In the sub electrode system 20 with the second reaction layer 53, the current value corresponded to the fructose concentration.

When the first and the second reaction layers 52 and 53 were dissolved in the sample liquid, the substrates in the sample liquid were respectively oxidized with the oxidoreductase specific to each layer. Pottasium ferricyanide was reduced into potassium ferrocyanide with an electron transfer in each layer. Next, by the application of the above predetermined voltages, an oxidation current value corresponding to the generated potassium ferrocyanide was obtained. The current value corresponded to the concentration of the substrate in the sample liquid.

The sensor response of the above saccharide sensor supplied with fruit juice as a sample liquid was measured. Glucose and fructose in the fruit juice could be quantified.

The GOD used in the first reaction layer 52 and the FDH used in the second reaction layer 53 have different pH conditions for providing the highest enzyme reactivity from each other. Generally, the most appropriate pH condition often depends upon a kind of the used enzyme. When the first and the second reaction layers 52 and 53 are provided on the same surface of the substrate 1, a buffering component contained in the second reaction layer 53 moves into the first reaction layer 52 containing the GOD by the dispersion of the sample liquid. Thus, the most appropriate pH condition may not be obtained. Further, the enzyme may move onto a plurality of electrodes by the dispersion of the sample liquid. Therefore, it is necessary to set a condition for not allowing the enzyme to move by immobilization or the like. As a result, the structure of the sensor can be limited.

When the reaction layers containing different enzymes are provided on the different surfaces of the insulating substrate 1 from each other as in this example, a component in each reaction layer can be prevented from moving when each reaction layer is dissolved in the sample liquid. In this way, the pH on each electrode system can be easily settled to be the most appropriate to the enzyme, and the enzyme can be freely dispersed in the sample liquid.

In the above described examples, when the cover and the spacer are made from a transparent material such as a transparent synthetic resin, it is possible to observe the condition of the reaction layer and the introducing condition of the sample liquid in the passage from the outside.

In the foregoing examples, in order to supply the sample liquid to the reaction layer more smoothly, a lecithin layer may be formed by developing an organic solvent solution of lecithin through the sample supply port into the reaction layer and drying thereof.

When the lecithin layer is provided, the sample liquid can be supplied even when the passage defined by the base, the cover and the spacer is not small enough to cause capillarity.

Since the amount of the sample liquid to be supplied depends upon the capacity of the passage, there is no need to previously quantify it. In addition, the evaporation of the sample liquid during the measurement can be minimized, thereby attaining a more accurate measurement.

The sample supply port is not necessarily distinguishable from the air port. It is possible to supply the sample liquid through the air port, using the sample supply port as an air port.

The oxidoreductase such as the GOD in the reaction layer is not especially immobilized to the main electrode system. However, since the reaction layer contains the hydrophilic polymer, the dispersion of the material is prevented due to increased viscosity of the sample liquid when the reaction layer is dissolved in the sample liquid. Therefore, the material making up the reaction layer does not move onto the sub electrode system in a short period of time. The enzyme can be effectively immobilized to conduct a more reliable measurement.

When the sample liquid is supplied through the sample supply port, it is effective to provide the sub electrode system in the vicinity of the sample supply port. In this way, the sample liquid proceeds toward the air port through the sample supply port. Therefore, a possibility for moving the oxidoreductase during the reaction toward the sub electrode system that is provided in the downstream of the flow of the sample liquid can be reduced. However, when the oxidoreductase is immobilized to the main electrode system, this does not cause any problem.

In Examples 5, 6 and 7, the sub electrode system has the same electrode pattern as the main electrode system. However, it does not have to be the same. For example, the pattern shown in FIG. 10 can be used.

There is no need to form all of the reaction layers, the first reaction layer, the second reaction layer and the reference layer in contact with the electrode systems as in the foregoing examples. When the base, the spacer and the cover are integrated, the reaction layer may be formed on a reverse surface of the cover and the like so as to face the passage.

Further, in the above-described examples, a method for quantifying glucose and fructose is shown. However, the present invention can be widely used in systems using an enzyme reaction, as an alcohol sensor, a lactic acid sensor, a cholesterol sensor and an amino acid sensor.

Moreover, in the foregoing examples, the GOD and the FDH are used as the oxidoreductase. However, alcohol oxidase, lactase oxidase, lactase dehydrogenase, cholesterol oxidase, xanthine oxidase and amino acid oxidase and the like can be used as well.

The hydrophilic polymer is not limited to the CMC used in the examples. Other cellulose derivatives such as hydroxy ethyl cellulose, hydroxy propyl cellulose, methyl cellulose, ethyl cellulose, ethyl hydroxy ethyl cellulose and carboxy methyl ethyl cellulose can be used. Moreover, the same effect can be attained by using polyvinylpyrrolidone, polyvinyl alcohol, gelatin or its derivatives, acrylic acid or its salts, methacrylic acid or its salts, starch or its derivatives and maleic anhydride or its salts.

As electron acceptors, apart from potassium ferricyanide used in the above-mentioned examples, p-benzoquinone, phenazinemethosulfate, methylene blue and ferrocene derivatives can be used.

Moreover, in the foregoing examples, the oxidoreductase and the electron acceptors are dissolved in the sample liquid. However, they may be immobilized to be insoluble in the sample liquid.

The above-described electrode system is not limited to a two-electrode system having only a working electrode and a counter electrode. A three-electrode system, including an additional reference electrode, may be used, so that more precise values are obtainable.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A biosensor comprising:
   an electrical insulating substrate,
   a main electrode system formed on the substrate and having a working electrode and a counter electrode,
   a reaction layer provided in contact with or in the vicinity of the main electrode system and containing an oxidoreductase, and
   a sub electrode system as a reference provided with an interval from the main electrode system and having a working electrode and a counter electrode, wherein a reference layer containing electron acceptors and a hydrophilic polymer is provided on the sub electrode system.

2. A biosensor according to claim 1, wherein the reaction layer further contains electron acceptors and a hydrophilic polymer.

3. A biosensor according to claim 1, wherein the oxidoreductase is selected from the group consisting of fructose dehydrogenase, glucose oxidase, alcohol oxidase, lactase oxidase, lactase dehydrogenase, cholesterol oxidase, xanthine oxidase and amino acid oxidase.

4. A biosensor according to claim 2, wherein the hydrophilic polymer is selected from the group consisting of carboxy methyl cellulose, hydroxy ethyl cellulose, hydroxy propyl cellulose, methyl cellulose, ethyl cellulose, ethyl hydroxy ethyl cellulose, carboxy methyl ethyl cellulose, polyvinylpyrrolidone, polyvinyl alcohol, gelatin or its derivatives, acrylic acid or its salts, methacrylic acid or its salts, starch or its derivatives, and maleic anhydride or its salts.

5. A biosensor according to claim 2, wherein the electron acceptors is selected from the group consisting of potassium ferricyanide, p-benzoquinone, phenazinemethosulfate, methylene blue and ferrocene.

6. A biosensor according to claim 1, wherein the main electrode system and the sub electrode system are provided on different surfaces of the substrate from each other, and the reaction layer is provided on the main electrode system.

7. A biosensor according to claim 1, wherein the counter electrode of the main electrode system is common to the counter electrode of the sub electrode system.

8. A biosensor according to claim 1, wherein the main electrode system is made from a material comprising carbon as a main component.

9. A biosensor according to claim 1, wherein the sub electrode system is made from a material comprising carbon as a main component.

10. A biosensor comprising:
    an electrical insulating substrate,
    a main electrode system formed on the substrate and having a working electrode and a counter electrode,
    a reaction layer provided on the main electrode system and containing an oxidoreductase and electron acceptors, and
    a sub electrode system as a reference provided with an interval from the main electrode system and the reaction layer and having a working electrode and a counter electrode, wherein a reference layer containing electron acceptors and a hydrophilic polymer is provided on the sub electrode system,
    wherein a substrate contained in a sample liquid is quantified by reducing the electron acceptors by electrons generated in a reaction of the substrate contained in the sample liquid and the oxidoreductase and then by electrochemically measuring the amount of the reduced electron acceptors.

11. A biosensor comprising:
    an electrical insulating substrate having a plurality of surfaces,
    a plurality of electrode systems formed on at least two surfaces of the substrate, each of the electrode systems having a working electrode and a counter electrode, and
    a plurality of reaction layers containing an oxidoreductase, respectively wherein the kinds of the one or more oxidoreductases contained in the reaction layers are different in every reaction layer
    wherein the electrode systems are respectively provided on different surfaces of the substrate from each other, and the reaction layers are provided on the same surfaces as the electrode systems.

12. A method for quantifying a substrate contained in a sample liquid by using a biosensor,
    the biosensor comprising an electrical insulating substrate, a main electrode system formed on the substrate and having a working electrode and a counter electrode, a reaction layer provided in contact with or in the vicinity of the main electrode system and containing an oxidoreductase, and a sub electrode as a reference provided on the substrate with an interval from the main electrode system and having a working electrode and a counter electrode, and the method comprising the steps of detecting a presence of the sample liquid on both the electrode systems by detecting a change of electrical characteristics between the main electrode system and the sub electrode system and then applying a voltage to the main electrode system and a sub electrode system, respectively.

13. A method for quantifying a substrate contained in a sample liquid by using a biosensor, the biosensor comprising an electrical insulating substrate, a main electrode system formed on the substrate and having a working electrode and a counter electrode, a reaction layer provided in contact with or in the vicinity of the main electrode system and containing an oxidoreductase, and a sub electrode system as a reference provided on the substrate with an interval from the main electrode system and having a working electrode and a counter electrode, and the method comprising the steps of detecting a change of electrical characteristics between the working electrode and the counter electrode in the main electrode system and the sub electrode system, respectively and determining a nature of the sample liquid on the basis of the difference of time required for detecting the electrical characteristics in the main and sub electrode systems.

* * * * *